United States Patent
Little, II et al.

[11] Patent Number: 6,143,516
[45] Date of Patent: Nov. 7, 2000

[54] IDENTIFICATION OF NOVEL ANTIMICROBIAL AGENTS USING MEMBRANE POTENTIAL INDICATOR DYES

[75] Inventors: Roger G. Little, II, Benicia; Susan Abrahamson, Albany; Peter Wong, Berkeley, all of Calif.

[73] Assignee: XOMA Technology Ltd., Berkeley, Calif.

[21] Appl. No.: 09/404,926

[22] Filed: Sep. 24, 1999

Related U.S. Application Data

[60] Provisional application No. 60/143,485, Jul. 12, 1999, provisional application No. 60/109,905, Nov. 25, 1998, and provisional application No. 60/101,778, Sep. 25, 1998.

[51] Int. Cl.[7] .............................. C12Q 1/02; C12Q 1/18; C12Q 1/00
[52] U.S. Cl. ................... 435/29; 435/32; 435/4; 435/911; 435/968; 549/227; 430/585
[58] Field of Search .................... 435/29, 32, 4, 435/911, 968; 549/227; 430/585

[56] References Cited

U.S. PATENT DOCUMENTS 4,859,584  8/1989  Horan et al. .............................. 435/29

OTHER PUBLICATIONS

Wang et al., "Susceptibility of Melanized and Nonmelanized *Crypotococcus neoformans* to the Melanin–Binding Compounds Trifluoperazine and Chloroquine"*Antimicrobial Agents and Chemotherapy* 40:541–545 (1996).

Abrahamson et al., "Mechanism of Action of XMP Antifungal Peptides: Factors that Influence Activity and Subcellular Localization", Abstract for ICAAC meeting, Sep. 28–Oct. 1, 1997, Toronto, Canada.

Little et al., "XMP Antifungal Peptides Demonstrate Enhanced Selectivity and Oral Availability" Abstract for ICAAC meeting, Sep. 24–27, 1998, San Diego, California.

*Primary Examiner*—Louise N. Leary
*Attorney, Agent, or Firm*—Marshall, O'Toole, Gerstein, Murray & Borun

[57] ABSTRACT

Novel screening methods for identifying antimicrobial agents involving use of membrane potential indicator dyes are provided.

11 Claims, 6 Drawing Sheets

SEQUENCE LISTING

```
<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: Modified site at C-Terminus; The C-Terminus is
      Amidated
<220> FEATURE:
<223> OTHER INFORMATION: Description of Artificial Sequence: artificial
      peptide XMP.391

<400> SEQUENCE: 1

Lys Val Gly Trp Leu Ile Gln Leu Phe His Lys Lys
  1               5                  10

<210> SEQ ID NO 2
<211> LENGTH: 12
<212> TYPE: PRT
<213> ORGANISM: Artificial Sequence
<220> FEATURE:
<223> OTHER INFORMATION: position 1 Xaa=D-Lys; position 2 Xaa=D-Val;
      position 11 Xaa=D-Lys; position 12 Xaa=D-Lys
<220> FEATURE:
<223> OTHER INFORMATION: Description of Artificial Sequence: artificial
      peptide XMP.445

<400> SEQUENCE: 2

Xaa Xaa Gly Trp Leu Ile Gln Leu Phe His Xaa Xaa
  1               5                  10
```

IDENTIFICATION OF NOVEL ANTIMICROBIAL AGENTS USING MEMBRANE POTENTIAL INDICATOR DYES

This application claims priority based on U.S. Provisional Application Serial No. 60/143,485 filed Jul. 12, 1999, U.S. Provisional Application Serial No. 60/109,905 filed Nov. 25, 1998, and U.S. Provisional Application Serial No. 60/101,778 filed Sep. 25, 1998.

FIELD OF THE INVENTION

The invention relates generally to screening methods involving use of membrane potential indicator dyes for identifying antimicrobial agents, including antifungal and antibacterial compounds.

BACKGROUND OF THE INVENTION

Fungi are not only important human and animal pathogens, but they are also among the most common causes of plant disease. Fungal infections (mycoses) are becoming a major concern for a number of reasons, including the limited number of antifungal agents available, the increasing incidence of species resistant to known antifungal agents, and the growing population of immunocompromised patients at risk for opportunistic fungal infections, such as organ transplant patients, cancer patients undergoing chemotherapy, burn patients, AIDS patients, or patients with diabetic ketoacidosis. The incidence of systemic fungal infections increased 600% in teaching hospitals and 220% in non-teaching hospitals during the 1980's. The most common clinical isolate is Candida albicans (comprising about 19% of all isolates). In one study, nearly 40% of all deaths from hospital-acquired infections were due to fungi. [Sternberg, Science, 266:1632–1634 (1994).]

Known antifungal agents include polyene derivatives, such as amphotericin B (including lipid or liposomal formulations thereof) and the structurally related compounds nystatin and pimaricin; flucytosine (5-fluorocytosine); azole derivatives (including ketoconazole, clotrimazole, miconazole, econazole, butoconazole, oxiconazole, sulconazole, tioconazole, terconazole, fluconazole, itraconazole, voriconazole [Pfizer] and SCH56592 [Schering-Plough]); allylamines-thiocarbamates (including tolnaftate, naftifine and terbinafine); griseofulvin; ciclopirox; haloprogin; echinocandins (including MK-0991 [Merck]); and nikkomycins. Recently discovered as antifungal agents are a class of products related to bactericidal/permeability-increasing protein (BPI), described in U.S. Pat. Nos. 5,627,153, 5,858,974, 5,652,332, 5,763,567 and 5,733,872, the disclosures of all of which are incorporated herein by reference.

Resistance of bacteria and other pathogenic organisms to antimicrobial agents is an increasingly troublesome problem. The accelerating development of antibiotic-resistant bacteria, intensified by the widespread use of antibiotics in farm animals and overprescription of antibiotics by physicians, has been accompanied by declining research into new antibiotics with different modes of action. [Science, 264: 360–374 (1994).]

Gram-positive bacteria have a typical lipid bilayer cytoplasmic membrane surrounded by a rigid cell wall that gives the organisms their characteristic shape, differentiates them from eukaryotic cells, and allows them to survive in osmotically unfavorable environments. This cell wall is composed mainly of peptidoglycan, a polymer of N-acetylglucosamine and N-acetylmuramic acid. In addition, the cell walls of gram-positive bacteria contain teichoic acids which are anchored to the cytoplasmic membrane through lipid tails, giving rise to lipoteichoic acids. The various substituents on teichoic acids are often responsible for the biologic and immunologic properties associated with disease due to pathogenic gram-positive bacteria. Most pathogenic gram-positive bacteria have additional extracellular structures, including surface polysaccharides, capsular polysaccharides, surface proteins and polypeptide capsules.

Gram-negative bacteria also have a cytoplasmic membrane and a peptidoglycan layer similar to but reduced from that found in gram-positive organisms. However, gram-negative bacteria have an additional outer membrane that is covalently linked to the tetrapeptides of the peptidoglycan layer by a lipoprotein; this protein also contains a special lipid substituent on the terminal cysteine that embeds the lipoprotein in the outer membrane. The outer layer of the outer membrane contains the lipopolysaccharide (LPS) constituent.

Antibacterial agents are generally directed against targets not present in mammalian cells. One major difference between bacterial and mammalian cells is the presence in bacteria of a rigid wall external to the cell membrane. Thus, chemotherapeutic agents directed at any stage of the synthesis, export, assembly, or cross-linking of peptidoglycan can lead to inhibition of bacterial cell growth and, in most cases, to cell death. These agents include bacitricin, the glycopeptides (vancomycin and teichoplanin), β-lactam antibiotics (penicillins, cephalosporins, carbapenems, and monobactams). Virtually all the antibiotics that inhibit bacterial cell wall synthesis are bactericidal. However, much of the loss of cell wall integrity following treatment with cell wall-active agents is due to the bacteria's own cell wall-remodeling enzymes (autolysins) that cleave peptidoglycan bonds in the normal course of cell growth. In the presence of antibacterial agents that inhibit cell wall growth, autolysis proceeds without normal cell wall repair; weakness and eventually cellular lysis occur. There are also antibacterial agents that do not affect cell wall synthesis but instead are believed to alter cell membrane permeability, such as the polymyxins (polymyxin B and colistin, or polymyxin E) and gramicidin A.

Another group of antibacterial agents are those that inhibit protein synthesis; most of these interact with the bacterial ribosome. The difference between the composition of bacterial and mammalian ribosomes gives these compounds their selectivity. These agents include the aminoglycosides (e.g., gentamicin, kanamycin, tobramycin, streptomycin, netilmicin, neomycin, and amikacin), the macrolides (e.g., erythromycin, clarithromycin, and azithromycin), the lincosamides (e.g., clindamycin and lincomycin), chloramphenicol, the tetracyclines (e.g., tetracycline, doxycycline, and minocycline) and mupirocin (pseudomonic acid).

Another group of antibacterial agents are antimetabolites that interfere with bacterial synthesis of folic acid. Inhibition of folate synthesis leads to cessation of cell growth and, in some cases, to bacterial cell death. The principal antibacterial antimetabolites are sulfonamides (e.g., sulfisoxazole, sulfadiazine, and sulfamethoxazole) and trimethoprim.

Yet a further group of antibacterial compounds affects nucleic acid synthesis or activity. These agents include the quinolones (e.g., nalidixic acid and its fluorinated derivatives norfloxacin, ciprofloxicin, ofloxacin, and lomofloxacin), which inhibit the activity of the A subunit of DNA gyrase, rifampin, nitrofurantoin, and metronidazole (which not only has activity against the electron transport system but also is believed to cause DNA damage).

BPI protein products are also described to have antibacterial activities in U.S. Pat. Nos. 5,198,541 and 5,523,288 and International Publication No. WO 95/08344 (PCT/US94/11255), all of which are incorporated by reference herein, disclosing activity against gram-negative bacteria, and U.S. Pat. Nos. 5,578,572 and 5,783,561 and International Publication No. WO 95/19180 (PCT/US95/00656), all of which are incorporated by reference herein, disclosing activity against gram-positive bacteria and mycoplasma, and co-owned, co-pending U.S. application Ser. No. 08/626,646, which is in turn a continuation of U.S. application Ser. No. 08/285,803, which is in turn a continuation-in-part of U.S. application Ser. No. 08/031,145 and corresponding International Publication No. WO 94/20129 (PCT/US94/02463), all of which are incorporated by reference herein, disclosing activity against mycobacteria.

BPI protein products have been shown to have additional antimicrobial activities. For example, U.S. Pat. No. 5,646,114 and International Publication No. WO 96/01647 (PCT/US95/08624), all of which are incorporated by reference herein, disclose activity of BPI protein products against protozoa.

Bactericidal/permeability-increasing protein (BPI) is a protein isolated from the granules of mammalian polymorphonuclear leukocytes (PMNs or neutrophils), which are blood cells essential in the defense against invading microorganisms. See Elsbach, 1979, *J. Biol. Chem.*, 254: 11000; Weiss et al., 1987, *Blood* 69: 652; Gray et al., 1989, *J. Biol. Chem.* 264: 9505. The amino acid sequence of the entire human BPI protein and the nucleic acid sequence of DNA encoding the protein (SEQ ID NOS: 2 and 3) have been reported in FIG. 1 of Gray et al., *J. Biol. Chem.*, 264:9505 (1989), incorporated herein by reference. Recombinant human BPI holoprotein has also been produced in which valine at position 151 is specified by GTG rather than GTC, residue 185 is glutamic acid (specified by GAG) rather than lysine (specified by AAG) and residue 417 is alanine (specified by GCT) rather than valine (specified by GTT). An N-terminal fragment of human BPI possesses the antibacterial efficacy of the naturally-derived 55 kD human BPI holoprotein. (Ooi et al., 1987, *J. Bio. Chem.* 262: 14891–14894). In contrast to the N-terminal portion, the C-terminal region of the isolated human BPI protein displays only slightly detectable anti-bacterial activity against gram-negative organisms and some endotoxin neutralizing activity. (Ooi et al., 1991, *J. Exp. Med.* 174: 649). An N-terminal BPI fragment of approximately 23 kD, referred to as rBPI$_{23}$, has been produced by recombinant means and also retains anti-bacterial, including anti-endotoxin activity against gram-negative organisms (Gazzano-Santoro et al., 1992, *Infect. Immun.* 60: 4754–4761). An N-terminal fragment analog designated rBPI$_{21}$ has been described in co-owned, co-pending U.S. Pat. No. 5,420,019.

Three separate functional domains within the recombinant 23 kD N-terminal BPI sequence have been discovered Little et al., 1994, *J. Biol. Chem.* 269: 1865). These functional domains of BPI designate regions of the amino acid sequence of BPI that contributes to the total biological activity of the protein and were essentially defined by the activities of proteolytic cleavage fragments, overlapping 15-mer peptides and other synthetic peptides. Domain I is defined as the amino acid sequence of BPI comprising from about amino acid 17 to about amino acid 45. Initial peptides based on this domain were moderately active in both the inhibition of LPS-induced LAL activity and in heparin binding assays, and did not exhibit significant bactericidal activity. Domain II is defined as the amino acid sequence of BPI comprising from about amino acid 65 to about amino acid 99. Initial peptides based on this domain exhibited high LPS and heparin binding capacity and exhibited significant antibacterial activity. Domain III is defined as the amino acid sequence of BPI comprising from about amino acid 142 to about amino acid 169. Initial peptides based on this domain exhibited high LPS and heparin binding activity and exhibited surprising antimicrobial activity, including antifungal and antibacterial (including, e.g., anti-gram-positive and anti-gram-negative) activity. The biological activities of peptides derived from or based on these functional domains (i.e., functional domain peptides) may include LPS binding, LPS neutralization, heparin binding, heparin neutralization or antimicrobial activity.

Of interest to the background of the present invention are dye indicators of membrane potential, which have been available for many years and have been employed to study cell physiology. These potentiometric dyes are organic compounds whose spectral properties are sensitive to changes in membrane potential. They can be classified generally into "fast" dyes, which can follow changes in potential in the millisecond range, and "slow" dyes, which generally operate by a potential-dependent partitioning between the extracellular medium and either the membrane or the cytoplasm. This partitioning of slow dyes occurs by redistribution of the dye via interaction of the voltage potential with ionic charge on the dye. Slow dyes include three general chromophore types: cyanines [such as Di-O-C6(3) and Di-S-C2(5)], oxonols [such as oxonol-VI and DiS-BaC2(3)] and rhodamines [such as rhodamine-123 and TMRE JPW-179]. [See Loew, Chapter 8 in *Biomembrane Electrochemistry*, Blank and Vodyanoy, eds., American Chemical Society, Washington, D.C. (1994), pages 151–173.]

The cyanine class of dyes are symmetrical molecules with delocalized positive charges. Depending on the nature of the dye and its concentration, the potential-dependent uptake can produce either an increase or a decrease in fluorescence intensity. In general, accumulation of the dye and membrane binding leads to enhancement of fluorescence. At high lipid-dye ratios, however, many of the cyanine dyes tend to aggregate, resulting in fluorescence self-quenching. Most carbocyanine dyes with short (C1–C6) alkyl chains stain mitochondria of live cells when used at low concentrations (~0.5 μM or ~0.1 μg/mL); those with pentyl or hexyl substituents also stain the endoplasmic reticulum when used at higher concentrations (~5–50 μM or ~1–10 μg/mL). The cyanine dye DiOC$_6$(3) (3,3'-dihexyloxacarbocyanine iodide) has less tendency to aggregate and displays an increased fluorescence quantum yield as it binds to the subcellular membranes. DiOC$_6$(3) is lipophilic and is often used as a stain for mitochondria and endoplasmic reticulum in eukaryotic cells.

The green fluorescent cyanine dye JC-1 (5,5',6,6'-tetrachloro-1,1',3,3'-tetraethylbenzimidazolylcarbocyanine halide; available as an iodide from Molecular Probes or as a chloride from Biotium, Inc.) exists as a monomer at low concentrations or at low membrane potential. However, at higher concentrations (aqueous solutions above 0.1 μM) or at higher potentials, JC-1 forms red fluorescent "J-aggregates" that exhibit a broad excitation spectrum of 485 to 585 nm and an emission maximum at ~590 nm. Emission from this dye has been used to investigate mitochondrial potentials in live cells by ratiometric techniques. Various types of ratio measurements are possible by combining signals from the monomer (absorption/emission maxima ~510/527 nm in water) and the J-aggregate. Optical filters designed for fluorescein and tetramethylrhodamine can be used to separately visualize the monomer and J-aggregate forms, respectively, or both forms can be observed simultaneously using a standard fluorescein longpass optical filter set.

The oxonols are anionic molecules that also show enhanced fluorescence upon binding to membranes. However, because of their negative charge, binding of oxonols is promoted by depolarization of the membrane. The negative charge of oxonols also lessens intracellular uptake and reduces their association with intracellular organelles.

Rhodamine-123 is a cell-permeant, cationic, fluorescent dye that is readily sequestered by active mitochondria without inducing cytotoxic effects. Uptake and equilibration of rhodamine-123 is rapid (a few minutes) compared to dyes such as DASPMI, which may take 30 minutes or longer, and this dye is especially suited for flow cytometry applications. Mitochondria stained with the dye appear yellow-green through a fluorescein longpass optical filter and red through a tetramethylrhodamine longpass optical filter. Unlike the lipophilic rhodamine and carbocyanine dyes, rhodamine 123 does not stain the endoplasmic reticulum. Rhodamine-123 has been used with a variety of cell types including nerve cells, bacteria, plant cells and spermatozoa, and has also been used to study apoptosis, axoplasmic transport of mitochondria, bacterial viability and vitality, mitochondrial enzymatic activities, transmembrane potential and other membrane activities, multidrug resistance, mycobacterial drug susceptibility and oocyte maturation. Derivatives of rhodamine-123 such as TMRE have been developed that are more permeable and have less hydrogen-bonding interaction with anionic sites in the mitochondrial inner membrane and matrix.

There continues to exist a need for novel antimicrobial agents useful for treating a variety of infections and for methods of identifying such novel compounds. Such methods ideally would provide for rapid and highly selective identification of compounds that may be structurally distinct from the major conventional antimicrobial agents.

SUMMARY OF THE INVENTION

The present invention generally provides methods for identifying antimicrobial compounds (including, for example, antifungal or antibacterial compounds) based on the discovery that a class of antimicrobial agents based on or derived from bactericidal/permeability-increasing protein (BPI) generates unique effects on fungal and bacterial cells as revealed by treatment with a cyanine membrane potential indicator dye, $DiOC_6(3)$. When BPI-derived peptide compounds are employed as antifungal agents, their effects are characterized by localization of the cyanine dye to mitochondria with increasing accumulation of this dye in a peptide concentration-dependent manner, and with retention of the dye notwithstanding an onset of loss or reduction of fungal cell viability at the same peptide concentration. The dye appears to be retained even after cell death has occurred (as confirmed, e.g., by a negative 24-hour growth culture or by use of other viability indicators, such as propidium iodide). Similarly, when $rBPI_{21}$ and BPI-derived peptide compounds are employed as antibacterial agents, their effects are also characterized by increasing accumulation of this cyanine dye in a peptide concentration-dependent manner, with retention of the dye notwithstanding an onset of loss or reduction of bacterial viability at the same peptide concentration.

Novel antimicrobial agents may be rapidly and selectively identified by screening test compounds for replication of the characteristic increase in dye fluorescence intensity produced by BPI protein products with continued retention of dye notwithstanding loss (i.e., reduction) of viability within the tested target cell population. Sources of test compounds include, for example, libraries (including combinatorial libraries) of inorganic and organic compounds (for example, bacterial, fungal, mammalian, insect or plant products, peptides, peptidomimetics and organomimetics). Presently preferred standard BPI-derived antimicrobial peptides that are known to produce this characteristic pattern include XMP.391 (SEQ ID NO:1) and XMP.445 (SEQ ID NO:2). This aspect of the invention thus contemplates a method of identifying an antimicrobial agent, particularly an antifungal compound, comprising the steps of (a) contacting a target cell (e.g., a fungal cell or a bacterial cell) with a test compound and with a membrane potential indicator dye, and (b) detecting an increasing accumulation of this dye and retention of this dye despite loss or reduction of target cell viability. Presently preferred membrane potential indicator dyes are $DiOC_6(3)$, JC-1, rhodamine-123 and MitoTracker Red CM-$H_2$Xros [M-7513, Molecular Probes, Inc., Eugene, Oreg.]. The concurrent loss or reduction of target cell viability may be confirmed by routine culture or through use of viability dyes, such as propidium iodide.

It is further contemplated that screening methods according to the present invention may involve multiple further stages of screening, including selection of test compounds that have a differential effect on target cells in comparison to non-target cells (e.g., a reduced effect on mammalian cells relative to fungal cells). This aspect of the invention provides a further screening assay involving (a) contacting a mammalian cell with the test compound and with the membrane potential indicator dye, and (b) detecting no substantial increase in dye fluorescence intensity. Optionally, compounds may be screened for selectivity for one type of microbial cell, e.g., selectivity for bacterial vs. fungal cells or vice versa.

Test compounds may be alternatively or additionally assayed for ability to kill or inhibit growth of target cells (e.g., fungal cells or bacteria) in vitro using any assays known in the art, including broth or radial diffusion assays. Suitable compounds may have a 2-fold, 10-fold, 50-fold, 100-fold, or greater separation (selectivity) between antimicrobial activity and mammalian cell activity. The most desirable compounds will preferably have a 50-fold or greater separation between antimicrobial activity and mammalian cell activity as quantified by differential effects on dye fluorescence intensity.

The in vivo antimicrobial activity of test compounds may also be assayed in any animal models of infection known to those skilled in the art. Such assays include those for in vitro and in vivo oral availability and those for in vivo oral activity as evidenced by activity when administered orally in a comparative survival study.

Another aspect of the invention provides kits for use in conducting the screening methods of the present invention. Such kits may optionally include (a) a membrane potential indicator and (b) a BPI-derived antimicrobial peptide or other BPI protein product suitable for use as a standard (positive control) against which the test compound may be compared.

The present invention also provides novel antimicrobial compounds identified by the screening methods of the present invention.

Yet a further aspect of the invention contemplates the treatment of infections, including fungal and bacterial infections, using compounds identified by the screening methods of the present invention that exhibit the above-described characteristic pattern, other than compounds known in the art (including BPI protein products such as BPI-derived peptides).

Numerous additional aspects and advantages of the invention will become apparent to those skilled in the art upon consideration of the following detailed description of the invention which describes presently prepared embodiments thereof.

DETAILED DESCRIPTION OF THE INVENTION

Figure 1:
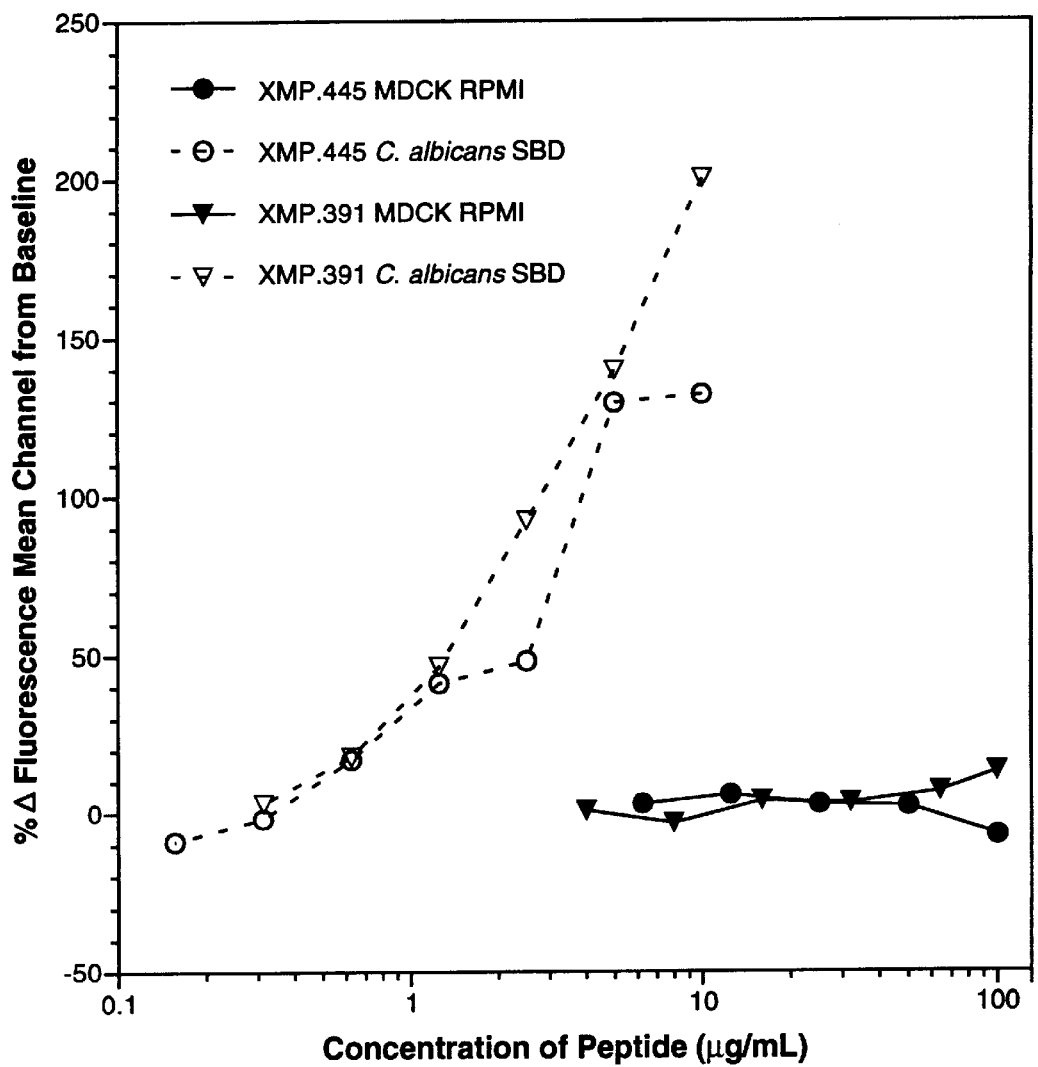
FIG. 1 depicts the effect of XMP.391 and XMP.445 on fungal and mammalian cells treated with cyanine dye $DiOC_6(3)$.

The present invention generally provides methods for identifying antimicrobial compounds that mimic the unique effects of BPI protein products, particularly BPI-derived antimicrobial peptides, on cells treated with a membrane potential indicator dye. This unique "fingerprint" manifests as a dose-dependent increase and accumulation of the membrane potential indicator dye by the target cells (as measured, for example, by an increase in dye fluorescence intensity) and retention of the dye despite the onset of loss or reduction of target cell viability. The invention is based on the discovery that antimicrobial agents based on or derived from bactericidal/permeability-increasing protein (BPI) display unexpectedly unique effects on fungal cells and bacteria treated with a cyanine membrane potential indicator dye, such as $DiOC_6(3)$. A characteristic pattern of peptide concentration-dependent dye accumulation in target cells with retention of the dye in the target cells at a time or peptide concentration when other indicators establish that the target cells have lost viability provides an unexpected "fingerprint." Dying target cells would not be expected to display an apparent increase in mitochondrial membrane potential and would not be expected to retain a membrane potential indicator dye.

Any membrane potential indicator dyes that provide the above-described unique "fingerprint" of BPI protein products, including any of the dyes named above (e.g., cyanine-, oxonol- or rhodamine-based dyes), may be used in the methods and kits of the present invention. For testing activity of compounds against eukaryotic cells such as fungal cells, preferred dyes are dyes that localize to mitochondria. For example, Haugland, *Handbook of Fluorescent Probes and Research Chemicals*, Spence, ed., Molecular Probes, Inc., Eugene, Oreg. (1996) lists a number of mitochondrial staining fluorescent dyes, including rhodamine 123 and rhodamine derivatives such as TMRM and TMRE, MitoTracker® Orange $CM-H_2TMRos$ and Red $CM-H_2Xros$ dyes [M-7511 and M-7513, Molecular Probes, Inc., Eugene, Oreg.]; carbocyanine dyes such as $DiOC_6(3)$, $DiOC_2(5)$, $DiOC_7(3)$, $DiSC_2(5)$, $DiSC_3(5)$ and $DiOC_5(3)$; styryl dyes such as DASPMI (4-Di-1-ASP and 2-Di-1-ASP) and DASPEI; JC-1 (5,5',6,6'-tetrachloro-1,1',3,3'-tetraethylbenzimidazolylcarbocyanine iodide) and its analogs such as TDBC-3 and TDBC-4. Presently preferred is cyanine dye $DiOC_6(3)$.

Any BPI protein product which displays the above-described characteristic pattern of increase in dye fluorescence intensity may be used as a standard against which the test compound may be compared. Presently preferred are $rBPI_{21}$ and BPI-derived peptides, including domain III-derived peptides such as XMP.391 (SEQ ID NO:1) [the structure of which is described in Table 1 of U.S. Pat. No. 5,858,974 and corresponding International Publication No. WO 97/04008 (PCT/US96/03845), both of which are incorporated by reference herein] and XMP.445 (SEQ ID NO:2) [the structure of which is described in co-owned, U.S. Provisional Application Serial Nos. 60/101,958 filed Sep. 25, 1998 and 60/109,896 filed Nov. 25, 1998, and co-owned, concurrently filed U.S. application Ser. No. 09/406,243 [Attorney Docket No. 27129/36272], all of which are incorporated by reference herein]. Procedures for the preparation and purification of BPI-derived peptides are described in, for example, U.S. Pat. Nos. 5,858,974, 5,733,872 and 5,652,332, incorporated herein by reference.

As used herein, "BPI protein product" includes naturally and recombinantly produced BPI protein; natural, synthetic, and recombinant biologically active polypeptide fragments of BPI protein; biologically active polypeptide variants of BPI protein or fragments thereof, including hybrid fusion proteins and dimers; biologically active polypeptide analogs of BPI protein or fragments or variants thereof, including cysteine-substituted analogs; and BPI-derived peptides; all of which are described in more detail in U.S. Pat. No. 5,627,153 and corresponding International Publication No. WO 95/19179 (PCT/US95/00498), both of which are incorporated herein by reference.

Test compounds may be assayed on any microbial organism, including those involved in pathogenic infection. Fungal species include, e.g., Candida (including *C. albicans, C. tropicalis, C. parapsilosis, C. stellatoidea, C. krusei, C. parakrusei, C. lusitanae, C. pseudotropicalis, C. guilliermondi* and *C. glabrata*), Aspergillus (including *A. fumigatus, A. flavus, A. niger, A. nidulans, A. terreus, A. sydowi, A. flavatus,* and *A. glaucus*), Cryptococcus, Histoplasma, Coccidioides, Paracoccidioides, Blastomyces, Basidiobolus, Conidiobolus, Rhizopus, Rhizomucor, Mucor, Absidia, Mortierella, Cunninghamella, Saksenaea, Pseudallescheria, Sporotrichosis, Fusarium, Trichophyton, Trichosporon, Microsporum, Epidermophyton, Scytalidium, Malassezia, Actinomycetes, Sporothrix, Penicillium, Saccharomyces and Pneumocystis. Gram-negative bacterial species that may be tested include Acidaminococcus, Acinetobacter, Aeromonas, Alcaligenes, Bacteroides, Bordetella, Branhamella, Brucella, Calymmatobacterium, Campylobacter, Cardiobacterium, Chromobacterium, Citrobacter, Edwardsiella, Enterobacter, Escherichia, Flavobacterium, Francisella, Fusobacterium, Haemophilus, Klebsiella, Legionella, Moraxella, Morganella, Neisseria, Pasturella, Plesiomonas, Proteus, Providencia, Pseudomonas, Salmonella, Serratia, Shigella, Streptobacillus, Veillonella, Vibrio, and Yersinia species; while gram-positive bacterial species that may be tested include Staphylococcus, Streptococcus, Micrococcus, Peptococcus, Peptostreptococcus, Enterococcus, Bacillus, Clostridium, Lactobacillus, Listeria, Erysipelothrix, Propionibacterium, Eubacterium, and Corynebacterium species. Protozoa include Plasmodia, Toxoplasma, Leishmania, Trypanosoma, Acanthamoeba, Nagleria, and Pneumocystis species.

Sources for test compounds to be screened include (1) inorganic and organic chemical libraries, (2) natural product libraries, and (3) combinatorial libraries comprised of either random or mimetic peptides, oligonucleotides or organic molecules. Chemical libraries may be readily synthesized or purchased from a number of commercial sources, and may include structural analogs of known compounds or compounds that are identified as "hits" or "leads" via natural product screening. The sources of natural product libraries are collections of microorganisms (including bacteria and fungi), animals, plants or other vegetation, insects, including Arachnid species, or marine organisms, and libraries of mixtures for screening may be created by: (1) fermentation and extraction of broths from soil, plant or marine microorganisms or (2) extraction of the organisms themselves. Natural product libraries include polyketides, non-ribosomal peptides, and variants (non-naturally occurring) variants thereof. For a review, see *Science* 282:63–68 (1998). Combinatorial libraries are composed of large numbers of peptides, oligonucleotides or organic compounds and can be readily prepared by traditional automated synthesis methods, PCR, cloning or proprietary synthetic methods. Of particular interest are peptide and oligonucleotide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, *Curr. Opin. Biotechnol.* 8:701–707 (1997). For reviews and examples of peptidomimetic libraries, see Al-Obeidi et al., *Mol. Biotechnol,* 9(3):205–23 (1998); Hruby et al., *Curr Opin Chem Biol,* 1(1):114–19 (1997); Dorner et al., *Bioorg Med Chem,* 4(5):709–15 (1996) (alkylated dipeptides). A variety of companies have constructed chemical libraries and provide their use for screening, including for example, 3-Dimensional Pharmaceuticals, Exton, Pa.; Agouron Pharmaceutical, La Jolla, Calif.; Alanex Corp., San Diego, Calif.; Ariad Pharmaceuticals, Cambridge, Mass.; ArQule, Inc., Medford, Mass.; Arris Pharmaceutical, S. San Francisco, Calif.; Axys, S. San Francisco, Calif.; Biocryst Pharmaceuticals, Birmingham, Ala.; Cadus Pharmaceuticals, Tarrytown, N.Y.; Cambridge Combinatorial, Cambridge, UK; ChemGenics, Cambridge, Mass.; CombiChem, San Diego, Calif.; Corvas International, San Diego, Calif.; Cubist Pharmaceuticals, Cambridge, Mass.; Darwin Molecular, Bothell, Wash.; Houghten Pharmaceuticals, San Diego, Calif.; Hybridon, Cambridge, Mass.; Isis Pharmaceuticals, Carlsbad, Calif.; Ixsys, San Diego, Calif.; Molecumetics, Bellevue, Wash.; Peptide Therapeutics, Cambridge, UK; Pharmacopia, Princeton, N.J.; SUGEN, Redwood City, Calif.; Telik, Inc., S. San Francisco, Calif.; and Tripos, Inc., St. Louis, Mo.

Preferably the compounds that are preliminarily identified by this method are then assayed by conventional methods known in the art for the ability to kill or inhibit growth/replication of whole target cells in vitro. Such assays may include the steps of contacting test compounds with whole target cells and measuring viability or proliferation of the target cells. Any assays known in the art may be used, including those described in Examples 2 and 3 of U.S. Pat. No. 5,858,974.

Some compounds may be more suitable for in vitro use, including, for example, use as a preservative or decontaminant for fluids and surfaces, or use to sterilize surgical and other medical equipment and implantable devices, either ex vivo or in situ, including prosthetic joints and indwelling invasive devices such as intravenous lines and catheters which are often foci of infection, or use in the preparation of growth media for non-target cells.

Ideally, the most desirable compounds for in vivo administration to mammals will have a differential effect on target and mammalian cells, i.e., if the compound does adversely affect mammalian cells, a higher concentration of the compound would be required to affect the mammalian cells in comparison to target cells, thereby providing a therapeutic window of suitable concentrations for administering the compound without undesirable toxic effects. The relative effect on target and mammalian cells may be determined using any in vitro assays known in the art, including by contacting mammalian cells with the same test compound and the same membrane potential indicator dye utilized for the initial antimicrobial screen, and selecting compounds that do not produce a substantial change in dye uptake.

The potential antimicrobial compounds may also be evaluated for their effect in any model of infection, including any in vivo model, known in the art. Exemplary animal models of fungal infection are described in Example 4 of U.S. Pat. No. 5,858,974 and may be modified for any fungal species (including Candida, Aspergillus and Fusarium). Other microbial infection models are known in the art. The most desirable compounds are capable of preventing the establishment of an infection or reversing the outcome of an infection once it is established without excessive toxicity.

The use of antimicrobial compounds identified by the screening methods of the present invention is contemplated for the treatment of subjects suffering from microbial infection, especially mammalian subjects such as humans, but also including farm animals such as cows, sheep, pigs, horses, goats and poultry (e.g., chickens, turkeys, ducks and geese), companion animals such as dogs and cats, exotic and/or zoo animals, and laboratory animals including mice, rats, rabbits, guinea pigs, and hamsters. Treatment of infection of plants is also contemplated. "Treatment" as used herein encompasses both prophylactic and therapeutic treatment, and may be accompanied by concurrent administration of other antimicrobial agents, including any of the agents discussed herein.

Therapeutic compositions may be administered systemically or topically. Systemic routes of administration include oral, intravenous, intramuscular or subcutaneous injection (including into a depot for long-term release), intraocular and retrobulbar, intrathecal, intraperitoneal (e.g. by intraperitoneal lavage), intrapulmonary (using powdered drug, or an aerosolized or nebulized drug solution), or transdermal. Suitable dosages include doses ranging from 1 $\mu$g/kg to 100 mg/kg per day and doses ranging from 0.1 mg/kg to 20 mg/kg per day. For polypeptide therapeutics that are amenable to administration via gene therapy, methods of delivering suitable genes to a subject (including plants and animals) are contemplated. Those skilled in the art can readily optimize effective dosages and administration regimens for therapeutic compositions as determined by good medical practice and the clinical condition of the individual subject.

"Concurrent administration," or "co-administration," as used herein includes administration of one or more agents, in conjunction or combination, together, or before or after each other. The agents may be administered by the same or by different routes. If administered via the same route, the agents may be given simultaneously or sequentially, as long as they are given in a manner sufficient to allow all agents to achieve effective concentrations at the site of action.

Known antifungal agents include polyene derivatives, such as amphotericin B (including lipid or liposomal formulations thereof) and the structurally related compounds nystatin and pimaricin; flucytosine (5-fluorocytosine); azole derivatives (including ketoconazole, clotrimazole, miconazole, econazole, butoconazole, oxiconazole, sulconazole, tioconazole, terconazole, fluconazole, itraconazole, voriconazole [Pfizer] and SCH56592 [Schering-Plough]); allylamines-thiocarbamates (including tolnaftate, naftifine and terbinafine); griseofulvin; ciclopirox; haloprogin; echinocandins (including MK-0991 [Merck]); and nikkomycins. Recently discovered as antifungal agents are a class of products related to bactericidal/permeability-increasing protein (BPI), described in U.S. Pat. Nos. 5,627,153, 5,858,974, 5,652,332, 5,763,567 and 5,733,872, the disclosures of all of which are incorporated herein by reference.

The polyene derivatives, which include amphotericin B and the structurally related compounds nystatin and pimaricin, are broad-spectrum antifungals that bind to ergosterol, a component of fungal cell membranes, and thereby disrupt the membranes. Amphotericin B is usually effective for systemic mycoses, but its administration is limited by toxic effects that include fever and kidney damage, and other accompanying side effects such as anemia, low blood pressure, headache, nausea, vomiting and phlebitis. The unrelated antifungal agent flucytosine (5-fluorocytosine), an orally absorbed drug, is frequently used as an adjunct to amphotericin B treatment for some forms of candidiasis and cryptococcal meningitis. Its adverse effects include bone marrow depression with leukopenia and thrombocytopenia.

The azole derivatives impair synthesis of ergosterol and lead to accumulation of metabolites that disrupt the function of fungal membrane-bound enzyme systems (e.g., cytochrome P450) and inhibit fungal growth. This group of agents includes ketoconazole, clotrimazole, miconazole, econazole, butoconazole, oxiconazole, sulconazole, tioconazole, terconazole, fluconazole and itraconazole. Significant inhibition of mammalian P450 results in significant drug interactions. Some of these agents may be administered to treat systemic mycoses. Ketoconazole, an orally administered imidazole, is used to treat nonmeningeal blastomycosis, histoplasmosis, coccidioidomycosis and paracoccidioidomycosis in non-immunocompromised patients, and is also useful for oral and esophageal candidiasis. Adverse effects include rare drug-induced hepatitis; ketoconazole is also contraindicated in pregnancy. Itraconazole appears to have fewer side effects than ketoconazole and is used for most of the same indications. Fluconazole also has fewer side effects than ketoconazole that is used for oral and esophageal candidiasis and cryptococcal meningitis. Miconazole is a parenteral imidazole with efficacy in coccidioidomycosis and several other mycoses, but has side effects including hyperlipidemia and hyponatremia.

The allylamines-thiocarbamates are generally used to treat skin infections. This group includes tolnaftate, naftifine and terbinafine. Another antifungal agent is griseofulvin, a fungistatic agent which is administered orally for fungal infections of skin, hair or nails that do not respond to topical treatment. Other topical agents include ciclopirox and haloprogin. [Chapter 49 in Goodman and Gilman, *The Pharmacological Basis of Therapeutics,* 9th ed., McGraw-Hill, New York (1996), pages 1175–1190.]

BPI protein products, a class of products related to bactericidal/permeability-increasing protein (BPI), are described in U.S. Pat. No. 5,627,153 and corresponding International Publication No. WO 95/19179 (PCT/US95/00498), all of which are incorporated by reference herein, to have antifungal activity. BPI-derived peptides with antifungal activity are described in U.S. Pat. No. 5,858,974, which is in turn a continuation-in-part of U.S. application Ser. No. 08/504,841 filed Jul. 20, 1994 and corresponding International Publication Nos. WO 96/08509 (PCT/US95/09262) and WO 97/04008 (PCT/US96/03845), all of which are incorporated by reference herein. Other peptides with antifungal activity are described in U.S. Pat. No. 5,652,332 [corresponding to International Publication No. WO 95/19372 (PCT/US94/10427)], and in U.S. Pat. Nos. 5,763,567 and 5,733,872 [corresponding to International Publication No. WO 94/20532 (PCT/US94/02465)], which is a continuation-in-part of U.S. patent application Ser. No. 08/183,222 filed Jan. 14, 1994, which is a continuation-in-part of U.S. patent application Ser. No. 08/093,202 filed Jul. 15, 1993 [corresponding to International Publication No. WO 94/20128 (PCT/US94/02401)], which is a continuation-in-part of U.S. patent application Ser. No. 08/030,644 filed Mar. 12, 1993, now U.S. Pat. No. 5,348,942, the disclosures of all of which are incorporated herein by reference.

Known antibacterial agents include antibiotics, which are natural chemical substances of relatively low molecular weight produced by various species of microorganisms, such as bacteria (including Bacillus species), actinomycetes (including Streptomyces) and fungi, that inhibit growth of or destroy other microorganisms. Substances of similar structure and mode of action may be synthesized chemically, or natural compounds may be modified to produce semi-synthetic antibiotics. These biosynthetic and semi-synthetic derivatives are also effective as antibiotics. The major classes of antibiotics are (1) the β-lactams, including the penicillins, cephalosporins and monobactams; (2) the aminoglycosides, e.g., gentamicin, tobramycin, netilmycin, and amikacin; (3) the tetracyclines; (4) the sulfonamides and trimethoprim; (5) the fluoroquinolones, e.g., ciprofloxacin, norfloxacin, and ofloxacin; (6) vancomycin; (7) the macrolides, which include for example, erythromycin, azithromycin, and clarithromycin; and (8) other antibiotics, e.g., the polymyxins, chloramphenicol and the lincosamides.

Antibiotics accomplish their anti-bacterial effect through several mechanisms of action which can be generally grouped as follows: (1) agents acting on the bacterial cell wall such as bacitracin, the cephalosporins, cycloserine, fosfomycin, the penicillins, ristocetin, and vancomycin; (2) agents affecting the cell membrane or exerting a detergent effect, such as colistin, novobiocin and polymyxins; (3) agents affecting cellular mechanisms of replication, information transfer, and protein synthesis by their effects on ribosomes, e.g., the aminoglycosides, the tetracyclines, chloramphenicol, clindamycin, cycloheximide, fucidin, lincomycin, puromycin, rifampicin, other streptomycins, and the macrolide antibiotics such as erythromycin and oleandomycin; (4) agents affecting nucleic acid metabolism, e.g., the fluoroquinolones, actinomycin, ethambutol, 5-fluorocytosine, griseofulvin, rifamycins; and (5) drugs affecting intermediary metabolism, such as the sulfonamides, trimethoprim, and the tuberculostatic agents isoniazid and para-aminosalicylic acid. Some agents may have more than one primary mechanism of action, especially at high concentrations. In addition, secondary changes in the structure or metabolism of the bacterial cell often occur after the primary effect of the antimicrobial drug.

The penicillins have a characteristic double-ring system composed of a β-lactam ring, which provides the antibacterial activity, and a thiazolidene ring. The penicillins are differentiated by a single side chain that is unique for each penicillin. The compounds are bactericidal and act by inhibiting bacterial transpeptidase, an enzyme involved in synthesis of the bacterial cell wall. Because of their mechanism of action, penicillins are generally active against growing, but not resting, cells. Penicillins, especially penicillin G, have largely gram-positive activity; the relative insensitivity of gram-negative rods to penicillin G and several other penicillins is probably due to the permeability barrier of the outer membrane of gram-negative bacteria. Ampicillin, carbenicillin, ticarcillin, and some other penicillins are active against gram-negative bacteria because they can pass through this outer membrane. Penicillins have relatively few adverse effects, the most important of which are the hypersensitivity (allergic) reactions. These compounds are widely distributed in the body, but do not enter cells and do not usually accumulate in CSF.

Bacterial resistance to the penicillins is by production of the enzyme β-lactamase, which catalyzes hydrolysis of the β-lactam ring. The percentage of bacteria resistant to penicillin has risen to about 80%. Several penicillins, including methicillin, oxacillin, cloxacillin, dicloxacillin and nafcillin, are not affected by the β-lactamase of staphylococci. These antibiotics are useful against most β-lactamase-producing species of Staphylococcus. However, a small number of species are resistant even to these penicillins. Some penicillins, amoxicillin and ticarcillin, are marketed in combination with clavulanic acid, which is a β-lactamase inhibitor that covalently binds to the enzyme and prevents it from hydrolyzing the antibiotics. Another inhibitor, sulbactam, is marketed in combination with ampicillin.

The cephalosporins are characterized by a β-lactam ring, like the penicillins, but have an adjacent dihydrothiazine ring instead of a thiazolidene ring. For convenience, these compounds are generally classified by generations. The first generation includes cephalothin, cephapirin, cefazolin, cephalexin, cephradine and cefadroxil. These drugs generally have excellent gram-positive activity except for enterococci and methicillin-resistant staphylococci, and have only modest gram-negative coverage. The second generation includes cefamandole, cefoxitin, ceforanide, cefuroxime, cefuroxime axetil, cefaclor, cefonicid and cefotetan. This generation generally loses some gram-positive activity by weight and gains limited gram-negative coverage. The third generation includes cefotaxime, moxalactam, ceftizoxime, ceftriaxone, cefoperazone and ceftazidime. These compounds generally sacrifice further gram-positive activity by weight but gain substantial gram-negative coverage against Enterobacter and sometimes are active against Pseudomonas. The cephalosporins bind to penicillin-binding proteins with varying affinity. Once binding occurs, protein synthesis is inhibited. Cephalosporins are usually well tolerated; adverse effects include hypersensitivity reactions and gastrointestinal effects. Cephalosporins may interact with nephrotoxic drugs, particularly aminoglycosides, to increase toxicity. Resistance to cephalosporins is mediated by several mechanisms, including production of β-lactamase, although some strains that do not produce β-lactamase are nevertheless resistant.

Imipenem is a N-formimidoyl derivative of the mold product thienamycin. It contains a β-lactam ring and somewhat resembles penicillin except for differences in the second ring. It has activity against both gram-positive and gram-negative organisms and is resistant to most β-lactamases, although not those from Pseudomonas. It is marketed in combination with cilastin, a compound that inhibits inactivation of imipenem in the kidney by renal dihydropeptidase I enzyme. Cilastin increases the concentration of imipenem in urine, although not in blood.

Aztreonam is the first of a new group of antibiotics referred to as the monobactams. These agents have a β-lactam ring but lack the second ring characteristic of the penicillins and cephalosporins. It acts by binding to penicillin-binding proteins, and produces long, filamentous bacterial shapes that eventually lyse. Aztreonam is active only against aerobic gram-negative bacteria, is susceptible to inactivation by some β-lactamases, and has few adverse effects.

The aminoglycosides contain amino sugars linked to an aminocyclitol ring by glycosidic bonds. They have similar mechanisms of action and properties, but differ somewhat in spectrum of action, toxicity, and susceptibility to bacterial resistance. The compounds are bactericidal, with activity against both gram-positive and gram-negative organisms, and act by binding to proteins on the 30S ribosome of bacteria and inhibiting protein synthesis. The aminoglycosides also bind to isolated LPS and have a very weak outer membrane permeabilizing effect. [Taber et al., *Microbiological Reviews* 53: 439–457 (1987)); Kadurugamuwa et al., *Antimicrobial Agents and Chemotherapy*, 37: 715–721 (1993); Vaara, *Microbiological Reviews* 56: 395–411 (1992)]. This class of antibiotics includes amikacin, gentamicin, kanamycin, neomycin, netilmycin, paromomycin and tobramycin. The aminoglycosides are usually reserved for more serious infections because of severe adverse effects including ototoxicity and nephrotoxicity. There is a narrow therapeutic window between the concentration required to produce a therapeutic effect, e.g., 8 μg/ml for gentamicin, and the concentration that produces a toxic effect, e.g., 12 μg/ml for gentamicin. Neomycin in particular is highly toxic and is never administered parenterally.

Tetracyclines have a common four-ring structure and are closely congeneric derivatives of the polycyclic naphthacenecarboxamide. The compounds are bacteriostatic, and inhibit protein synthesis by binding to the 30S subunit of microbial ribosomes and interfering with attachment of aminoacyl tRNA. The compounds have some activity against both gram-positive and gram-negative bacteria; however, their use is limited because many species are now relatively resistant. Adverse effects include gastrointestinal effects, hepatotoxicity with large doses, and nephrotoxicity in some patients. This antibiotic class includes tetracycline, chlortetracycline, demeclocycline, doxycycline, methacycline, minocycline and oxytetracycline.

The sulfonamides are derivatives of sulfanilamide, a compound similar in structure to para-aminobenzoic acid (PABA), which is an essential precursor for bacterial synthesis of folic acid. The compounds are generally bacteriostatic, and act by competitively inhibiting incorporation of PABA into tetrahydrofolic acid, which is a required cofactor in the synthesis of thymidines, purines and DNA. Sulfonamides have a wide range of activity against gram-positive and gram-negative bacteria, but their usefulness has diminished with increasingly high prevalence of bacterial resistance. The sulfonamide class of antibiotics includes sulfacytine, sulfadiazine, sulfamethizole, sulfisoxazole, sulfamethoxazole, sulfabenzamide and sulfacetamide. Adverse effects include hypersensitivity reactions and occasional hematological toxicity.

Trimethoprim is an inhibitor of the dihydrofolate reductase enzyme, which converts dihydrofolic to tetrahydrofolic acid, a required factor for DNA synthesis. Adverse effects include gastrointestinal distress and rare hematological toxicity. Trimethoprim is also available in combination with sulfamethoxazole (also known as co-trimoxazole). The combination is usually bactericidal, although each agent singly is usually bacteriostatic. The combination is the drug of choice for Salmonella infections, some Shigella infections, *E. coli* traveler's diarrhea and *Pneumocystis carinii* pneumonia.

The fluoroquinolones and quinolones are derivatives of nalidixic acid, a naphthyridine derivative. These compounds are bactericidal, and impair DNA replication, transcription and repair by binding to the DNA and interfering with DNA gyrase, an enzyme which catalyzes negative supercoiling of DNA. The fluoroquinolones, which include norfloxacin, ciprofloxacin, and ofloxacin, and the quinolones, which include cinoxacin, have a broad spectrum of antimicrobial activity against gram-negative and gram-positive organisms. These compounds distribute widely through extravascular tissue sites, have a long serum half-life, and present few adverse effects. Because of their effect on DNA, the drugs are contraindicated in pregnant patients and in children whose skeletal growth is incomplete.

Vancomycin is a glycopeptide, with a molecular weight of about 1500, produced by a fungus. It is primarily active against gram-positive bacteria. The drug inhibits one of the final steps in synthesis of the bacterial cell wall, and is thus effective only against growing organisms. It is used to treat serious infections due to gram-positive cocci when penicillin G is not useful because of bacterial resistance or patient allergies. Vancomycin has two major adverse effects, ototoxicity and nephrotoxicity. These toxicities can be potentiated by concurrent administration of another drug with the same adverse effect, such as an aminoglycoside.

The macrolides are bacteriostatic and act by binding to the 50S subunit of 70S ribosomes, resulting in inhibition of protein synthesis. They have a broad spectrum of activity against gram-positive and gram-negative bacteria and may be bacteriostatic or bactericidal, depending on the concentration achieved at sites of infection. The compounds distribute widely in body fluids. Adverse effects include gastrointestinal distress and rare hypersensitivity reactions. The most common macrolide used is erythromycin, but the class includes other compounds such as clarithromycin and azithromycin.

The polymyxins are a group of closely related antibiotic substances produced by strains of *Bacillus polymyxa*. These drugs, which are cationic detergents, are relatively simple, basic peptides with molecular weights of about 1000. Their antimicrobial activity is restricted to gram-negative bacteria. They interact strongly with phospholipids and act by penetrating into and disrupting the structure of cell membranes. Polymyxin B also binds to the lipid A portion of endotoxin and neutralizes the toxic effects of this molecule. Polymyxin B has severe adverse effects, including nephrotoxicity and neurotoxicity, and should not be administered concurrently with other nephrotoxic or neurotoxic drugs. The drug thus has limited use as a therapeutic agent because of high systemic toxicity, but may be used for severe infections, such as *Pseudomonas aeruginosa* meningitis, that respond poorly to other antibiotics.

Chloramphenicol inhibits protein synthesis by binding to the 50S ribosomal subunit and preventing binding of aminoacyl tRNA. It has a fairly wide spectrum of antimicrobial activity, but is only reserved for serious infections, such as meningitis, typhus, typhoid fever, and Rocky Mountain spotted fever, because of its severe and fatal adverse hematological effects. It is primarily bacteriostatic, although it may be bactericidal to certain species.

Lincomycin and clindamycin are lincosamide antimicrobials. They consist of an amino acid linked to an amino sugar. Both inhibit protein synthesis by binding to the 50S ribosomal subunit. They compete with erythromycin and chloramphenicol for the same binding site but in an overlapping fashion. They may be bacteriostatic or bactericidal, depending on relative concentration and susceptibility. Gastrointestinal distress is the most common side effect. Other adverse reactions include cutaneous hypersensitivity, transient hematological abnormalities, and minor elevations of hepatic enzymes. Clindamycin is often the drug of choice for infections caused by anaerobic bacteria or mixed aerobic/anaerobic infections, and can also be used for susceptible aerobic gram-positive cocci.

Some drugs, e.g. aminoglycosides, have a small therapeutic window. For example, 2 to 4 $\mu$g/ml of gentamicin or tobramycin may be required for inhibition of bacterial growth, but peak concentrations in plasma above 6 to 10 $\mu$g/ml may result in ototoxicity or nephrotoxicity. These agents are more difficult to administer because the ratio of toxic to therapeutic concentrations is very low. Antimicrobial agents that have toxic effects on the kidneys and that are also eliminated primarily by the kidneys, such as the aminoglycosides or vancomycin, require particular caution because reduced elimination can lead to increased plasma concentrations, which in turn may cause increased toxicity. Doses of antimicrobial agents that are eliminated by the kidneys must be reduced in patients with impaired renal function. Similarly, dosages of drugs that are metabolized or excreted by the liver, such as erythromycin, chloramphenicol, or clindamycin, must be reduced in patients with decreased hepatic function.

Bacteria acquire resistance to antibiotics through several mechanisms: (1) production of enzymes that destroy or inactivate the antibiotic [Davies, *Science*, 264:375–381 (1994)]; (2) synthesis of new or altered target sites on or within the cell that are not recognized by the antibiotic [Spratt, *Science*, 264:388–393 (1994)]; (3) low permeability to antibiotics, which can be reduced even further by altering cell wall proteins, thus restricting access of antibiotics to the bacterial cytoplasmic machinery; (4) reduced intracellular transport of the drug; and (5) increased removal of antibiotics from the cell via membrane-associated pumps [Nikaido, *Science*, 264:382–387 (1994)].

The susceptibility of a bacterial species to an antibiotic is generally determined by two microbiological methods. A rapid but crude procedure uses commercially available filter paper disks that have been impregnated with a specific quantity of the antibiotic drug. These disks are placed on the surface of agar plates that have been streaked with a culture of the organism being tested, and the plates are observed for zones of growth inhibition. A more accurate technique, the broth dilution susceptibility test, involves preparing test tubes containing serial dilutions of the drug in liquid culture media, then inoculating the organism being tested into the tubes. The lowest concentration of drug that inhibits growth of the bacteria after a suitable period of incubation is reported as the minimum inhibitory concentration.

The resistance or susceptibility of an organism to an antibiotic is determined on the basis of clinical outcome, i.e., whether administration of that antibiotic to a subject infected by that organism will successfully cure the subject. While an organism may literally be susceptible to a high concentration of an antibiotic in vitro, the organism may in fact be resistant to that antibiotic at physiologically realistic concentrations. If the concentration of drug required to inhibit growth of or kill the organism is greater than the concentration that can safely be achieved without toxicity to the subject, the microorganism is considered to be resistant to the antibiotic. To facilitate the identification of antibiotic resistance or susceptibility using in vitro test results, the National Committee for Clinical Laboratory Standards (NCCLS) has formulated standards for antibiotic susceptibility that correlate clinical outcome to in vitro determinations of the minimum inhibitory concentration of antibiotic.

Other aspects and advantages of the present invention will be understood upon consideration of the following illustrative examples. Example 1 addresses the effect of two BPI-derived peptides, XMP.391 and XMP.445, on fungal cells and mammalian cells treated with the cyanine membrane potential indicator dye, $DiOC_6(3)$. Example 2 addresses the concurrent effect of these same BPI-derived peptides on fungal cells treated with propidium iodide (PI), an indicator of cell viability. Example 3 addresses in vitro oral absorption screening of BPI-derived peptides and Example 4 addresses in vivo oral absorption screening of BPI-derived peptides. Example 5 addresses the in vivo oral activity of XMP.445 in a mouse survival efficacy study. Example 6 addresses the effect of the antifungal agent miconazole on fungal cells and mammalian cells treated with $DiOC_6(3)$. Example 7 addresses the effect of BPI-derived peptides on fungal cells treated with the membrane potential indicator dyes JC-1, dihydrorhodamine 123, $DiOC_6(3)$ and MitoTracker® Red CM-$H_2$Xros. Example 8 shows localization of the accumulation of membrane potential indicator dye using confocal microscopy. Example 9 addresses the effect of a BPI protein product on bacteria treated with $DiOC_6(3)$.

EXAMPLE 1

Effect of XMP.391 and XMP.445 on Fungal and Mammalian Cells Treated with $DiOC_6(3)$ The relative effect of two BPI-derived peptides, XMP.391 and XMP.445, on fungal and mammalian cells treated with the cyanine membrane potential indicator dye $DiOC_6(3)$ (3,3'-dihexyloxacarbocyanine iodide) [Molecular Probes, Inc., Eugene, Oreg.], was assessed as follows.

A stock fungal cell suspension was prepared as follows. Fungi (*Candida albicans* strain SLU#1) were cultured on Sabouraud's dextrose agar plates [1 L water, 10 g neopeptone, 20 g dextrose, 15 g Bacto Agar]. One or two colonies from the agar plate were inoculated into 5 mL of Sabouraud's dextrose broth (SDB) [1 L water, 10 g neopeptone, 20 g dextrose] in a sterile 10 mL polypropylene tube and incubated for about 18 hours at 30° C. After this incubation, 4 mL of the fungal culture was inoculated into a flask containing 100 mL of SDB and incubated for about 5 hours or until log growth phase was reached. The culture was centrifuged at 3000 rpm for 5 minutes (Sorvall RT6000B centrifuge), the supernatant was decanted and the pellets were resuspended in a total of 30 mL of SDB. Fungal cell concentration was determined either by absorbance at 570 nm or by diluting 1:10 with Trypan Blue and counting the number of fungal cells using a hemacytometer. The suspension was diluted with SDB to obtain a stock fungal cell suspension of approximately $1-2\times10^6$ CFU/mL Stock 1 mg/mL solutions of peptides XMP.391 and XMP.445 were prepared in saline, and six 2-fold serial dilutions were prepared using phosphate buffered saline (PBS). The fungal cell suspension was divided into 1 mL aliquots, and approximately 20 μL of each serial dilution of XMP.391 or XMP.445 peptide solution was added to an aliquot of fungal cell suspension to obtain final peptide concentrations of 0.313, 0.625, 1.25, 2.5, 5, 10 and 20 μg/mL in the aliquots. No peptide solution was added to the auto-fluorescence and baseline controls. The aliquots were incubated for 1 hour at 30° C. After the incubation, all aliquots were centrifuged at 3000 rpm for 5 minutes (Sorvall RT6000B) and the supernatant removed. The auto-fluorescence control aliquot was resuspended in 1 mL of SDB; the remainder of the samples and the baseline control were resuspended in 1 mL of 10 ng/mL $DiOC_6(3)$/SDB. The auto-fluorescence control thus contained fungal cells in SDB alone (without XMP peptide and without dye), while the baseline control contained fungal cells with dye (but without XMP peptide). After a 20 to 30 minute incubation in the dark at 30° C., the samples and controls were centrifuged, the SDB was removed, and the pellets were resuspended in 1 mL of PBS.

The samples were analyzed for fluorescence on the FAC-Scan flowcytometer [Becton-Dickinson, Mountain View, Calif.] using the $fl_1$ detector at a wavelength of 530 nm using the following parameters:

|  | Amplifier | Detector |
| --- | --- | --- |
| FSC | 1.00–2.00 | E00 |
| SSC | 1.00–2.00 | 200–300 |
| FL1 (530 nm) | Log | 400–500 |
| FL2 (585 nm) | Log | 400–500 |

The auto-fluorescence control was used for gating and fluorescence sensitivity was determined using the baseline control. The percent change in fluorescent intensity, expressed as mean channels, was determined by dividing the difference between the sample and baseline values by the baseline value: (sample $fl_1$–baseline $fl_1$)/baseline $fl_1\times100$.

The same procedure was also carried out using mammalian Madin-Derby canine kidney epithelial (MDCK) cells (ATCC Accession No. CCL34). The MDCK cells were cultured until confluent in MEM media supplemented with 10% fetal calf serum (FCS) and L-glutamine. The cells were harvested and resuspended to approximately $1-2\times10^6$ cells/mL in RPMI media, treated with XMP.391 or XMP.445 at concentrations varying from 5 μg/mL to 100 μg/mL, and incubated for 1 hour. The cells were then stained with $DiOC_6(3)$ for 30 minutes and fluorescence intensity was determined in the same manner as described above for *C. albicans*.

The results, displayed graphically in FIG. 1 as percent change in fluorescence mean channel from baseline vs. concentration of XMP peptide, show that treatment of the *C. albicans* cells with XMP peptide and $DiOC_6(3)$ dye resulted in a concentration-dependent increase in fluorescence intensity with increasing concentration of XMP peptide, despite a loss of fungal cell viability that occurs at a peptide concentration of about 2 μg/mL for XMP.391 and about 4 μg/mL for XMP.445. In separate experiments, XMP.391 and XMP.445 were shown to have minimum fungicidal concentration values of 2 μg/mL and 4 μg/mL, respectively, against this *C. albicans* SLU#1 strain.

Loss of fungal cell viability after XMP peptide treatment was confirmed not only by increased propidium iodide uptake as described in Example 2 below but also by culture, which showed no detectable fungal cell growth after the aliquots were incubated for 24 hours. Even after 24 hours, the aliquots were observed to retain their increased fluorescence intensity.

In contrast, treatment of the MDCK cells with the two XMP peptides and $DiOC_6(3)$ dye resulted in no substantial increase in fluorescence intensity even at 100-fold higher concentrations of XMP peptide. These results demonstrate that peptides XMP.391 and XMP.445 show a selective effect on fungal cells in comparison to mammalian cells.

EXAMPLE 2

Effect of XMP.391 and XMP.445 on Fungal and Mammalian Cells Treated with PI

Figure 2:
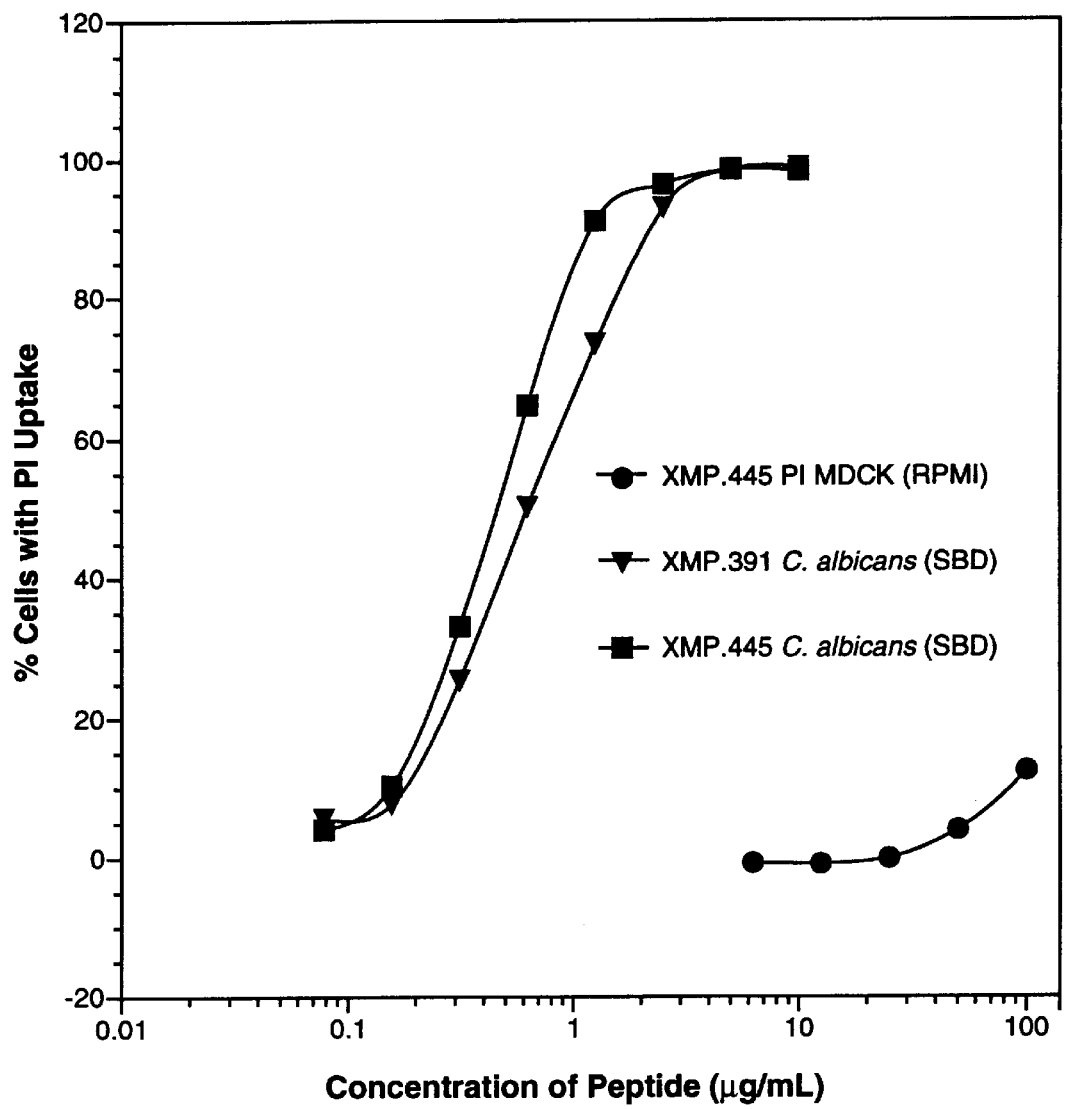
FIG. 2 depicts the effect of XMP.391 and XMP.445 on fungal cells treated with propidium iodide and the effect of XMP.445 on mammalian cells treated with propidium iodide.

The effect of two BPI-derived peptides, XMP.391 and XMP.445, on fungal cells (*C. albicans* SLU#1) treated with a viability dye, propidium iodide (PI) (Sigma, St. Louis, Mo.), and the effect of XMP.445 on mammalian MDCK cells treated with PI, was assessed generally according to Example 1 above, except that after the initial 1-hour incubation, samples and controls (including a baseline control and a positive control) were resuspended in 1 mL of 10 µg/mL propidium iodide/Dulbecco's PBS rather than 10 ng/mL $DiOC_6(3)$/SDB and stained for 20 minutes in the dark at room temperature. As in Example 1, the auto-fluorescence control contained fungal or mammalian cells in media alone (without XMP peptide and without PI), while the baseline control contained fungal or mammalian cells with PI (but without XMP peptide). Because it is a viability dye, PI is taken up only when cells are dying or dead; the fluorescent intensity of PI-treated samples should increase with the number of dead cells and should be maximal with 100% dead cells. Thus, for this experiment, a positive control was also prepared (containing 100% dead cells) by resuspending cells in 1 mL of 70% ethanol during the last 10 minutes of the initial 1-hour incubation; this positive control thus contained 100% dead cells with PI (but without XMP peptide). Samples were analyzed for PI uptake on the FACScan using the $fl_2$ detector at a wavelength of 585 nm. The auto-fluorescence sample was used for gating, while the fluorescence sensitivity was determined by the positive control and the PI uptake threshold was determined by the baseline control. The percent change in fluorescent intensity in mean channels was determined using the same equation used in Example 1, and the percentage of cells with PI uptake (i.e., dead cells) was calculated. The results are displayed graphically in FIG. 2 as percent of cells with PI uptake vs. concentration of peptide. These results, taken together with FIG. 1, confirm that treatment with XMP.391 and XMP.445 resulted in increasing accumulation of dye in fungal cells (as measured by increased dye fluorescence intensity) and retention of dye despite reduction of fungal cell viability or fungal cell death. These results also show that XMP.445 did not substantially affect viability of mammalian cells, even at a concentration of 50-fold or greater.

EXAMPLE 3

In Vitro Oral Absorption Screening

Various BPI-derived peptides were screened for oral absorption in in vitro screening assays using CACO-2 and MDCK cells. Cultured monolayers of CACO-2 (Human colon carcinoma) [Audus, K. L., et al. *Pharm. Res.*, 7: 435–451 (1990)] or Madin-Derby canine kidney epithelial (MDCK) cells (ATCC Accession No. CCL34) were grown upon collagen-coated, permeable-filter supports (Becton Dickenson, Mountainview, Calif.). The cells were grown to confluency and allowed to differentiate. The integrity of the monolayers was determined by measuring the transepithelial resistance. The cells were incubated with peptide on the apical side for 2.5 hours in MDCK screening or 4 hours for CACO-2 screening. The transepithelial transport of the peptide was measured by quantitative HPLC analysis of the incubation media on the basolateral side of the cells. Radiolabelled mannitol and cortisone were used as positive controls.

Intestinal absorption screening of peptides XMP.365, XMP.391 and XMP.445 identified XMP.445 as a potential orally available compound.

EXAMPLE 4

In Vivo Oral Absorption Screening

Various BPI-derived peptides are screened for oral absorption in an in vivo screening assay in which the peptides are administered by oral gavage to mice. Serum concentrations of the peptides are measured at various time intervals after administration by HPLC. Specifically, peptides are administered to mice at dosages of either 10 mg/kg body weight or 20 mg/kg body weight and the serum concentrations are measured at intervals of 1 hour 4 hours and 24 hours after administration to the mice. Peptide analysis indicates absorption after oral administration and serum concentrations achieved.

EXAMPLE 5

Oral Activity of XMP.445

XMP.445 was tested for activity upon oral administration (oral activity) in a 28-day comparative survival efficacy study in mice systemically infected with *Candida albicans*. Specifically, male DBA/2 mice (Charles River Laboratories) six weeks of age were dosed with $7.9 \times 10^4$ *Candida albicans*, SLU-1 in 100 µl intravenously via the tail vein in a single dosage on day 0. Treatment began immediately thereafter with 400 µl oral gavage of either 0.5% dextrose, or XMP.445 in 0.5% dextrose at levels of either 10 mg/kg or 20 mg/kg every other day for a total of eight times. Amphotericin B (Fungizone®) was administered intravenously at 0.5 mg/kg as a positive control every other day for a total of eight times. Twice-day monitoring (once daily on weekends and holidays) for mortality was performed. The animals treated with XMP.445 showed improvements in mortality compared with the dextrose-treated controls, and the animals treated with XMP.445 at 10 mg/kg showed significant improvement (p-value of 0.025). The results of this study show that XMP.445 has oral antifungal activity.

EXAMPLE 6

Effect of Miconazole on Fungal and Mammalian Cells Treated with $DiOC_6(3)$

Figure 3:
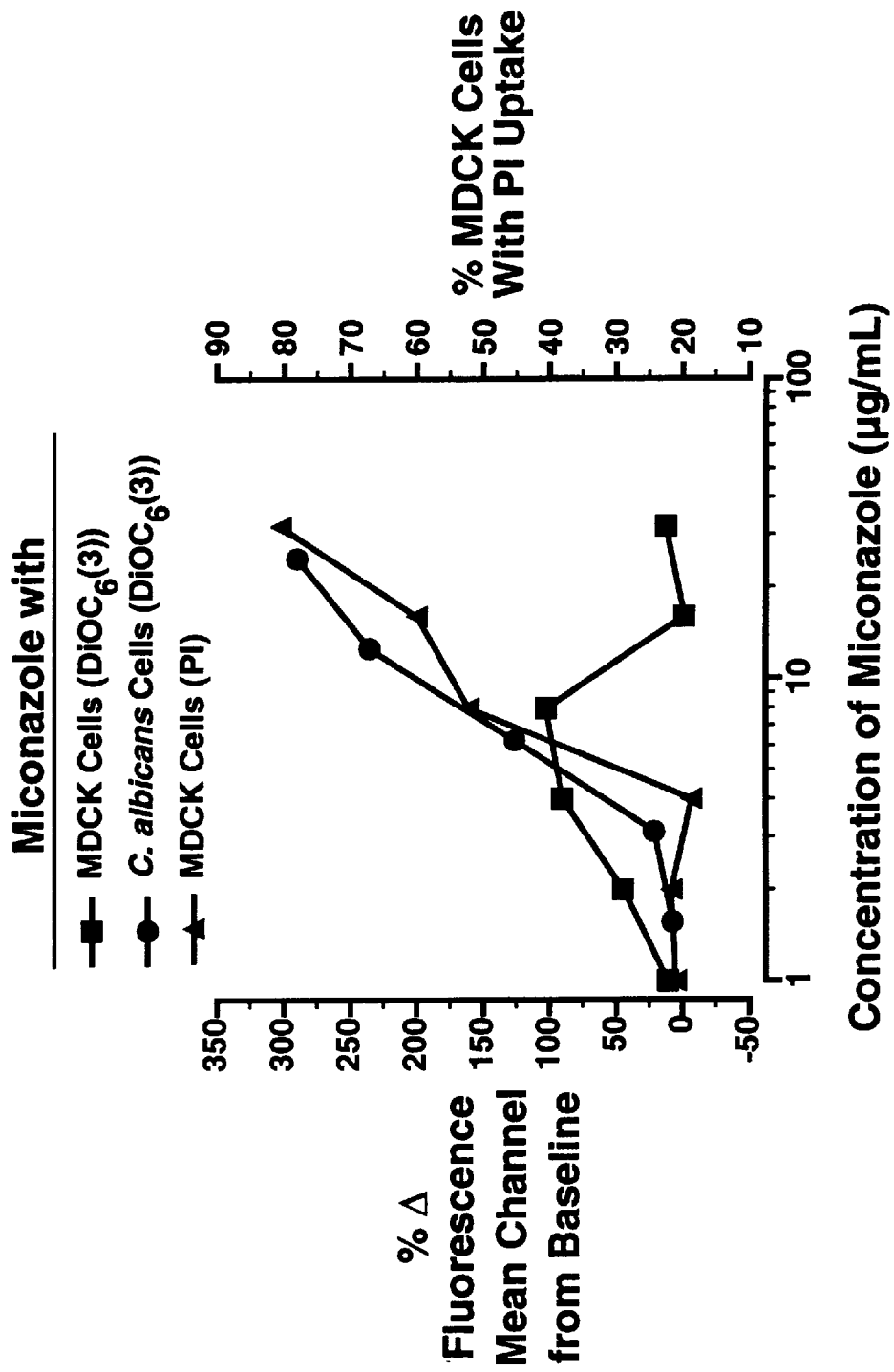
FIG. 3 depicts the effect of miconazole on fungal and mammalian cells treated with $DiOC_6(3)$ and on mammalian cells treated with propidium iodide.

The relative effect of varying concentrations of the antifungal agent miconazole on fungal *C. albicans* cells treated with membrane potential indicator dye $DiOC_6(3)$ [Molecular Probes], mammalian MDCK cells treated with $DiOC_6(3)$ and mammalian MDCK cells treated with PI, was assessed as described above in Examples 1 and 2, except that fungal *C. albicans* or mammalian MDCK cells were resuspended to a concentration of $1 \times 10^6$ cells/mL The results, displayed graphically in FIG. 3 as percent change in fluorescence mean channel from baseline vs. concentration of miconazole, show that treatment of the *C. albicans* cells with miconazole and $DiOC_6(3)$ dye resulted in a concentration-dependent increase in fluorescence intensity with increasing concentration of miconazole despite a loss of fungal cell viability that occurs at a miconazole concentration of less than or equal to about 1 µg/mL. These results show that treatment with miconazole resulted in accumulation of dye in fungal cells (as measured by increased dye fluorescence intensity) and retention despite reduction of fungal cell viability or fungal cell death, confirming that other known antifungal agents produce the pattern or "fingerprint" characteristic of the BPI-derived peptides XMP.391 and XMP.445. However, miconazole treatment produces a similar pattern of DiOC6(3) fluorescence increase in mammalian cells, indicating a lack of selective effect for fungal vs. mammalian cells and a significant toxicity for mammalian cells. This toxicity is confirmed by the results of treating the MDCK cells with miconazole and PI, which produced an increase in fluorescence intensity indicating cell death.

EXAMPLE 7

Effect of XMP.391 and XMP.445 on Fungal Cells Treated with a Variety of Membrane Potential Indicator Dyes The relative effect of varying concentrations of BPI-derived peptide XMP.391 on fungal *C. albicans* cells treated with a variety of membrane potential indicator dyes was evaluated.

The membrane potential indicator dyes JC-1 (5,5',6,6'-tetrachloro-1,1',3,3'-tetraethylbenzimidazolylcarbocyanine iodide, also called $CBIC_2(3)$); dihydrorhodamine 123; $DiOC_6(3)$; and MitoTracker® Red CM-$H_2$Xros (M-7513; $C_{32}H_{33}ClN_2O$) [all dyes obtained from Molecular Probes] were evaluated at concentrations of 10 µg/mL JC-1, 10 µg/mL dihydrorhodamine 123, 10 ng/mL $DiOC_6(3)$ and 1 µg/mL MitoTracker® Red CM-$H_2$Xros.

Experiments were carried out as described above in Example 1. FL1 (530 nm) was used to measure emission of $DiOC_6(3)$; FL2 (585 nm) was used to measure emission of rhodamine-123 and MitoTracker® Red CM-$H_2$Xros; and both FL1 and FL2 were used to measure the emission ratio of JC-1/J-aggregate, at an excitation of 488 nm.

Figure 4:
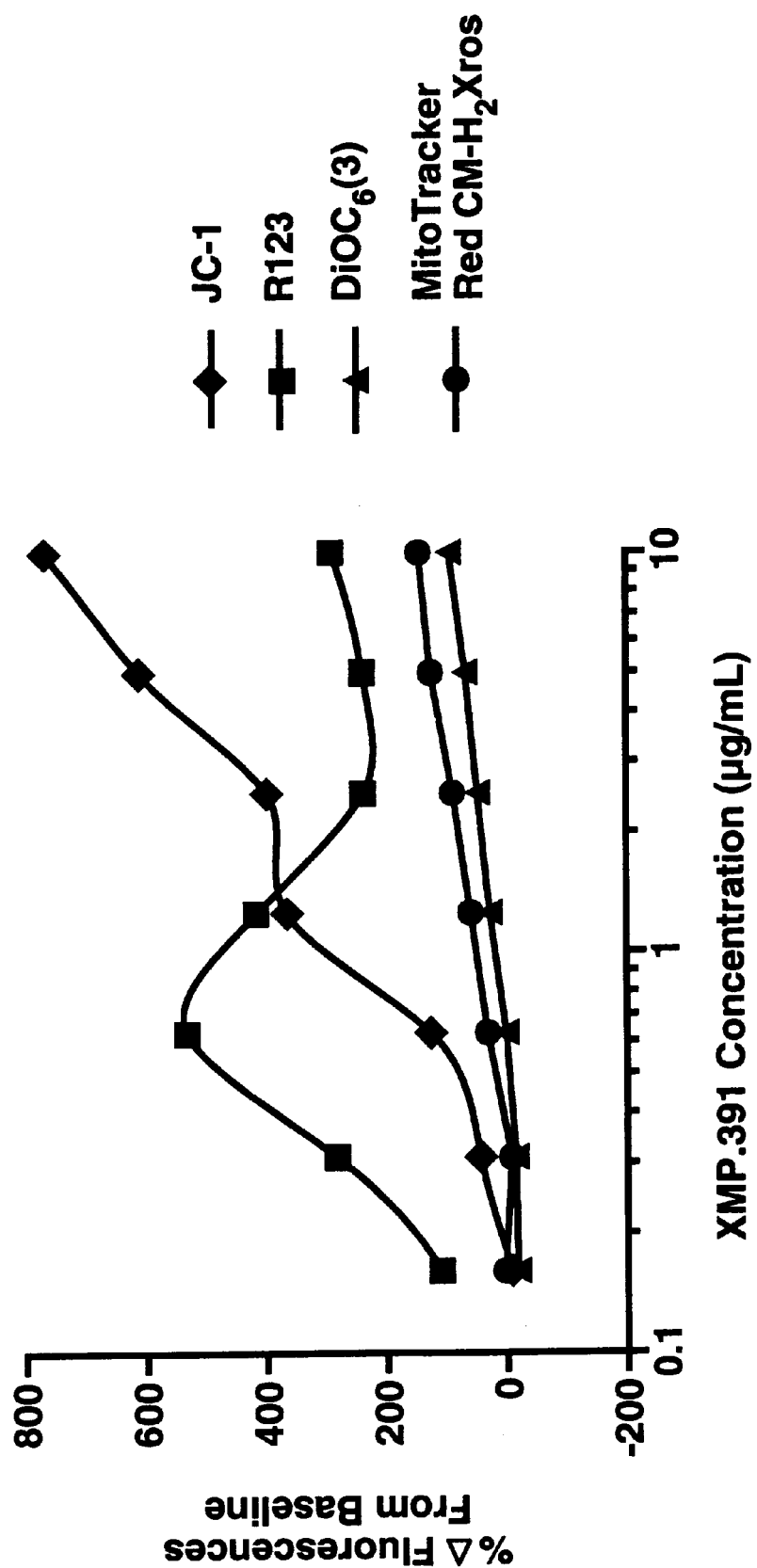
FIG. 4 depicts the effect of XMP.391 on fungal cells treated with a variety of membrane potential indicator dyes.

Results are displayed graphically in FIG. 4 and show that all four of these dyes produce the characteristic pattern of XMP.391 peptide concentration-dependent dye accumulation and retention in mitochondria. In this experiment, JC-1 and rhodamine 123 produced the highest rise in dye fluorescence intensity, primarily because higher concentrations of the dye can be used without adverse effects on mitochondrial specificity or fungal cell viability.

Similar results were obtained when experiments were carried out using XMP.445 and either $DiOC_6(3)$ or MitoTracker® Red CM-$H_2$Xros dyes.

EXAMPLE 8

Localization of the Accumulation of Membrane Potential Indicator Dye

The effect of the BPI-derived peptides XMP.391 and XMP.445 on fungal cells treated with a membrane potential indicator dye was further examined using confocal microscopy as follows. Confocal microscopy provides focused fluorescence detection, one plane or slice at a time, at a focus level that allows unobstructed localization of fluorescence within cells. A suspension of $1 \times 10^6$ fungal cells/mL was prepared as described above in Example 1 and 1 mL was dispensed into each of four Eppendorf microcentrifuge tubes. Two µL of 1 mg/mL XMP.445 (in saline) was added to two tubes and all four tubes were incubated for 1 hour at 30° C. After the incubation, all tubes were centrifuged in an Eppendorf 5415 centrifuge. The supernatant was removed and the pellet resuspended in 1 mL of SDB. The membrane potential indicator dye $DiOC_6(3)$ (diluted in SDB from a stock solution of 2 mg/mL in EtOH) was added to one set of peptide-treated and untreated tubes to a final concentration of 10 ng/mL. The membrane potential indicator dye MitoTracker™ Red CM-$H_2$Xros (from a freshly prepared solution of 500 µg/mL in DMSO) was added to another set of peptide-treated and untreated tubes to a final concentration of 1 µg/mL. The tubes were incubated at 30° C. for 30 min. After the incubation the tubes were centrifuged and the supernatant removed. The pellets were resuspended in 100 µL of 30% glycerol/PBS solution. Three µL from each tube was pipetted onto a microscope slide with a No. 1 cover glass and placed onto a Zeiss 510 Confocal Microscope that uses LSM Version 2.01 software. The 10× objective lens was used to isolate and focus on the yeast, then the 100× oil immersion lens was used to do the confocal microscopy. The following were the approximate settings for the confocal microscope: Laser: 488 nm for $DiOC_6(3)$, or 568 nm for MitoTracker™ Red CM-$H_2$Xros; Scan Mode: Stack; Pixel Dept: 8 bit; Stack Size: $1024 \times 1024 \times 16$, 40.7 µm×40.7 µm×3.8 µm; Pixel time: 88 µs; Objective 100× Plan-Apochomat 1.4 oil immersion lens; Beam Splitter: MBS HFT 488 for $DiOC_6(3)$ or 568 for MitoTracker Red™ CM-$H_2$Xros); DBS1: None; DBS2: Mirror; DBS3: None; Laser power 43%; Filter: BP 505–550 for $DiOC_6(3)$ or LP 585 for MitoTracker™ Red CM-$H_2$Xros); Pinhole: Ch1 93 µm. The scanned images were stored in TIFF format and is reconstructed and projected with the LSM 510 software loaded on the Zeiss microscope.

Under these conditions, an average of 10 to 20 cells can be detected per picture. The effect of XMP.391 was also examined using the same procedure. The results showed that in the XMP.391-treated and XMP.445-treated fungal cells, as compared to untreated cells, there was a visually observable increased fluorescence intensity that was localized at the mitochondria.

EXAMPLE 9

Effect of a BPI Protein Product on Bacteria Treated With $DiOC_6(3)$

Figure 5:
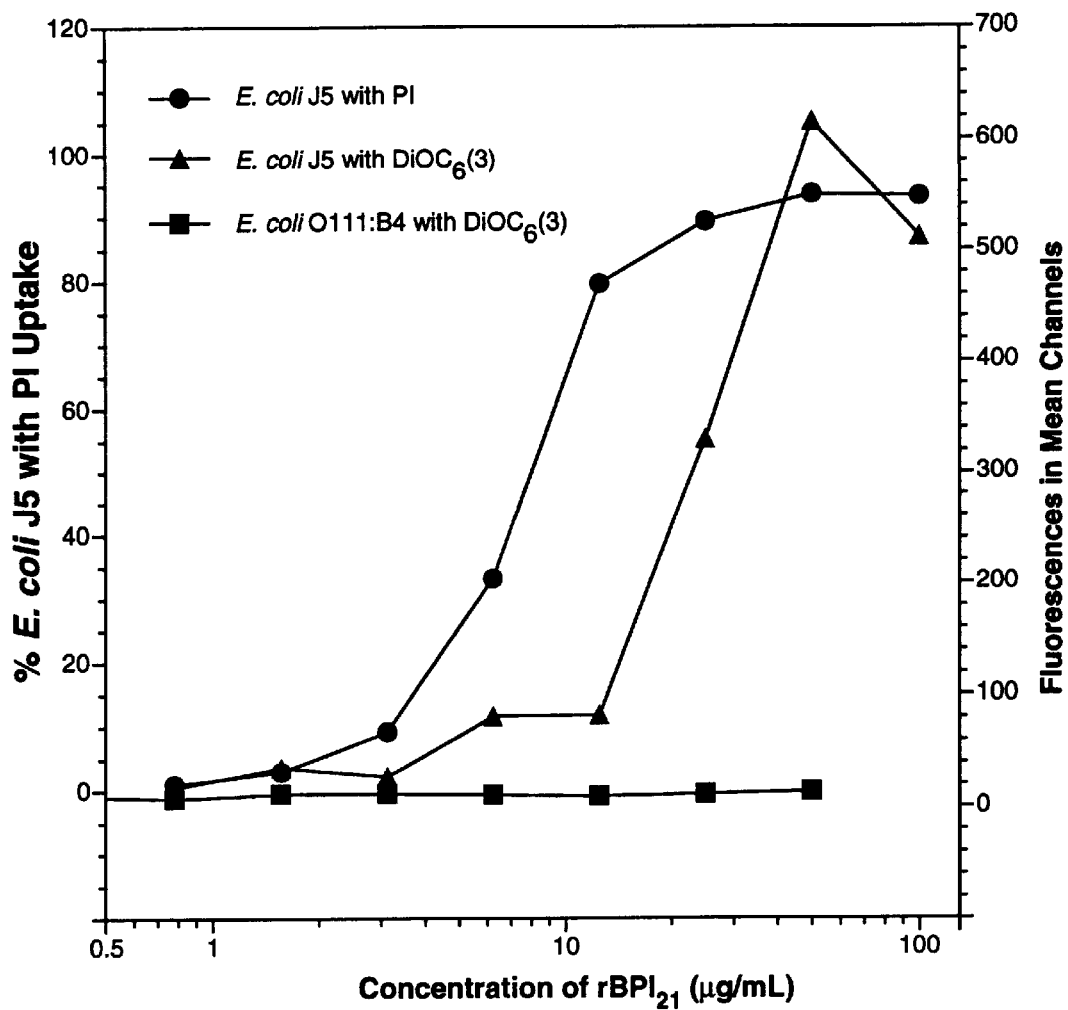
FIG. 5 depicts the effect of $rBPI_{21}$ on *E. coli* J5 cells treated with cyanine dye $DiOC_6(3)$ and propidium iodide and on *E. coli* O111 cells treated with $DiOC_6(3)$.
Figure 6:
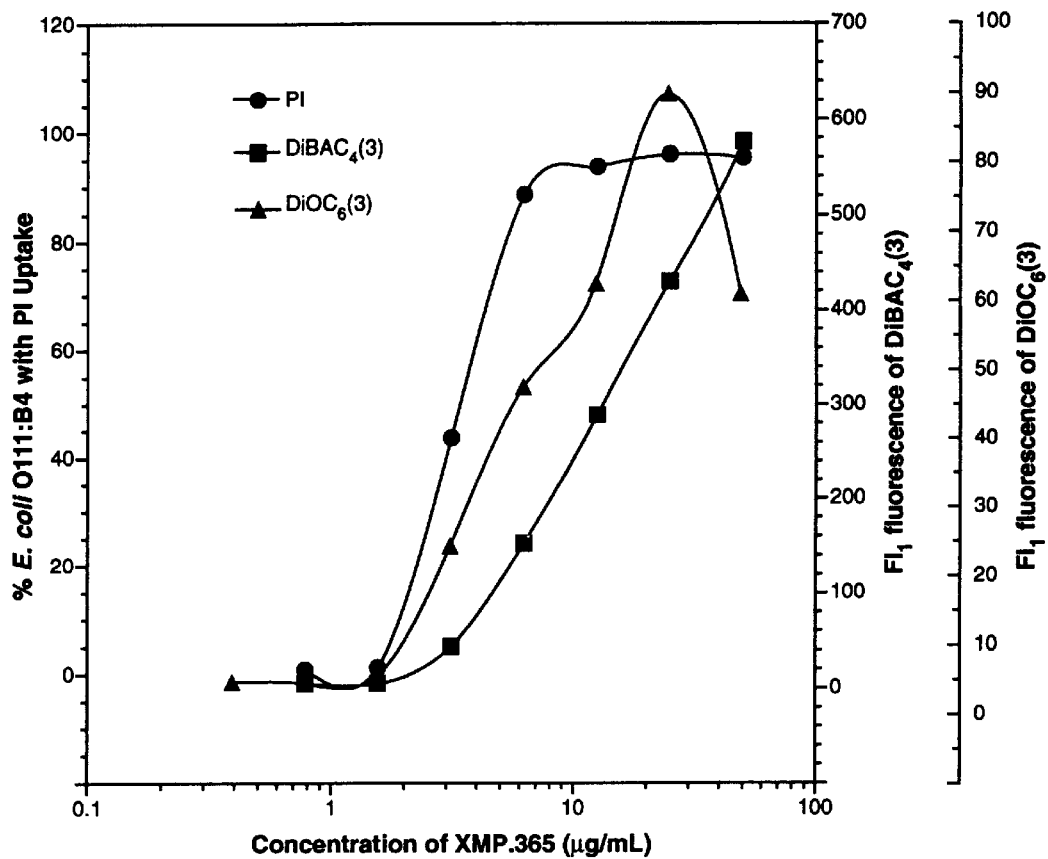
FIG. 6 depicts the effect of XMP.365 on *E. coli* cells treated with cyanine dye $DiOC_6(3)$ and propidium iodide.

The results of experiments carried out as described above in Example 1 using $DiOC_6(3)$ showed that treatment of *E. coli* J5 with $rBPI_{21}$ (which has in vitro bactericidal activity against this strain) produced an increasing accumulation of the dye that was retained despite decreased cell viability, while treatment of *E. coli* O111:B4 with $rBPI_{21}$ (which does not have in vitro bactericidal activity against this strain) did not produce an accumulation and retention of the dye. Results are displayed in FIG. 5, in which the triangles represent treatment of *E. coli* J5 with $rBPI_{21}$ and $DiOC_6(3)$, the circles represent treatment of *E. coli* J5 with $rBPI_{21}$ and propidium iodide, and the squares represent treatment of *E. coli* O111:B4 with $rBPI_{21}$ and $DiOC_6(3)$ The results of further experiments with $DiOC_6(3)$ showed that treatment of *E. coli* O111:B4 with XMP.365 [the structure of which is described in U.S. Pat. No. 5,858,974] (which has in vitro bactericidal activity against this strain) produced an increasing accumulation of the dye that was retained despite decreased cell viability. Results are shown in FIG. 6, in which the triangles represent treatment of bacteria with XMP.365 and DiOC$_6$(3), the squares represent treatment of E. coli O111:B4 with XMP.365 and DiBAC(3), and circles represent treatment of E. coli O111:B4 with XMP.365 and propidium iodide.

Numerous modifications and variations of the above-described invention are expected to occur to those of skill in the art. Accordingly, only such limitations as appear in the appended claims should be placed thereon.

(b) detecting an increasing accumulation of said dye and retention of dye despite reduction of microbial cell viability.

4. The method of any one of claims 1 through 3 further comprising the step of determining microbial cell viability.

5. The method of any one of claims 1 through 3 further comprising the steps of:

(a) contacting a mammalian cell with said test compound and with said membrane potential indicator dye, and (b) detecting no substantial change in dye uptake.

What is claimed is:

1. A method of identifying an antifungal compound comprising the steps of:

(a) contacting fungal cells with a test compound and with a membrane potential indicator dye, and (b) detecting an increasing accumulation of said dye and retention of dye despite reduction of fungal cell viability.

2. A method of identifying an antibacterial compound comprising the steps of:

(a) contacting bacterial cells with a test compound and with a membrane potential indicator dye, and (b) detecting an increasing accumulation of said dye and retention of dye despite reduction of bacterial cell viability.

3. A method of identifying an antimicrobial compound comprising the steps of:

(a) contacting microbial cells with a test compound and with a membrane potential indicator dye, and 6. The method of any one of claims 1 through 3 further comprising the step of assaying said test compound for the ability to inhibit growth of microbial cells or to kill microbial cells.

7. The method of any one of claims 1 through 3 further comprising the steps of assaying said test compound for in vivo oral availability or oral activity.

8. The method of any one of claims 1 through 3 wherein said membrane potential indicator dye is DiOC$_6$(3) (3,3'-dihexyloxacarbocyanine iodide).

9. The method of any one of claims 1 through 3 wherein said membrane potential indicator dye is JC-1 (5,5',6,6'-tetrachloro-1,1',3,3'-tetraethylbenzimidazolylcarbocyanine halide, or CBIC$_2$(3)).

10. The method of any one of claims 1 through 3 wherein said membrane potential indicator dye is dihydrorhodamine 123.

11. The method of any one of claims 1 through 3 wherein said membrane potential indicator dye is MitoTracker® Red CM-H$_2$Xros (M-7513; C$_{32}$H$_{33}$ClN$_2$O).

* * * * *